United States Patent [19]

Plöger et al.

[11] 4,108,961
[45] Aug. 22, 1978

[54] PROCESS OF STABILIZATION OF ANHYDROUS DIBASIC CALCIUM PHOSPHATE AGAINST FLUORINE IONS WITH AZACYCLOALKANE-2,2-DIPHOSPHONIC ACIDS

[75] Inventors: Walter Plöger, Hilden; Claus Gutzschebauch, Neuss, both of Fed. Rep. of Germany

[73] Assignee: Henkel Kommanditgesellschaft auf Aktien, Dusseldorf-Holthausen, Fed. Rep. of Germany

[21] Appl. No.: 636,736

[22] Filed: Dec. 1, 1975

[30] Foreign Application Priority Data

Nov. 30, 1974 [DE] Fed. Rep. of Germany ....... 2456808

[51] Int. Cl.² ...................... C01B 15/16; C01B 25/26
[52] U.S. Cl. ................................ 423/265; 423/308; 424/57; 423/311
[58] Field of Search ............................... 423/299–323, 423/308–311, 265, 268; 424/49, 52, 57, 128

[56] References Cited

U.S. PATENT DOCUMENTS 3,941,772  3/1976  Ploger et al. ...................... 424/57 X

*Primary Examiner*—O. R. Vertiz
*Assistant Examiner*—Gregory A. Heller
*Attorney, Agent, or Firm*—Hammond & Littell

[57] ABSTRACT

A process for stabilizing anhydrous dibasic calcium phosphate against reaction with fluorine ions comprising treating an aqueous suspension of anhydrous dibasic calcium phosphate at a pH of from 5 to 10 with an azacycloalkane-2,2-diphosphonic acid of the formula

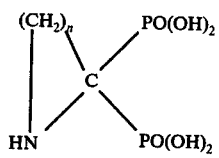

wherein $n$ is an integer from 3 to 5, or a water-soluble salt thereof, in an amount of from 0.01% to 5% by weight with reference to the anhydrous dibasic calcium phosphate; as well as tooth cleaning preparation containing the stabilized anhydrous dibasic calcium phosphate.

5 Claims, No Drawings

PROCESS OF STABILIZATION OF ANHYDROUS DIBASIC CALCIUM PHOSPHATE AGAINST FLUORINE IONS WITH AZACYCLOALKANE-2,2-DIPHOSPHONIC ACIDS

RELATED ART

Anhydrous dibasic calcium phosphate having the formula CaHPO$_4$ is a polishing substance frequently utilized in tooth cleaning preparations as, for example, toothpastes and powders. For this purpose it may be used alone or in admixture with other polishing substances as, for example, silica gel or plastics cleaning substances. If soluble fluorides or other compounds providing fluorine ions are added to these tooth cleaning preparations as anti-caries substances, the fluorine contained therein may be inactivated by conversion into the soluble and inactive calcium fluoride. The process thereby occurring may be represented by the following empirical reaction:

CaHPO$_4$ + 2 NaF → CaF$_2$ + Na$_2$HPO$_4$

The speed of this inactivation reaction is influenced by several circumstances such as temperature, pH value of the mixture and its composition.

For the use of a polishing agent as cleaning material in toothcleaning preparations, its abrasive behavior is of decisive importance, since products to be used for this purpose must only have an abrasive power which does not cause damage to the teeth. Owing to its favorable abrasive behavior, anhydrous dibasic calcium phosphate already enjoys great popularity as a cleaning material in tooth cleaning preparations. Its property of making the fluorine-containing compounds used for control of caries in the tooth cleaning preparation inactive or at least strongly reducing their action is, however, extremely undesirable. The problem, therefore, exists of finding ways and means largely to stop this inactivation of the fluorine-containing added substances.

OBJECTS OF THE INVENTION

An object of the present invention is the development of a process for stabilizing anhydrous dibasic calcium phosphate against reaction with fluorine ions consisting essentially of suspending anhydrous dibasic calcium phosphate in an aqueous medium at a pH of from 5 to 10, containing from 0.01% to 5% by weight based on the content of dibasic calcium phosphate of an azacycloalkane-2,2-diphosphonic compound selected from the group consisting of (A) compounds of the formula

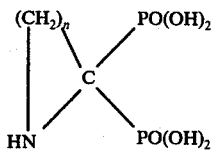

wherein $n$ is an integer from 3 to 5, and (B) water-soluble salts thereof, and separating said stabilized anhydrous dibasic calcium phosphate.

Another object of the present invention is the obtaining of a stabilized anhydrous dibasic calcium phosphate.

A further object of the present invention is the obtaining of tooth cleaning preparations containing a stabilized anhydrous dibasic calcium phosphate.

These and other objects of the present invention will become more apparent as the description thereof proceeds.

DESCRIPTION OF THE INVENTION

It has now been found that a satisfactory and easily effected stabilization of anhydrous dibasic calcium phosphate against reactions with fluorine ions is possible by treating the anhydrous dibasic calcium phosphate in aqueous medium at a pH of from 5 to 10, preferably from 6 to 8, with an azacycloalkane-2,2-diphosphonic acid of the general formula

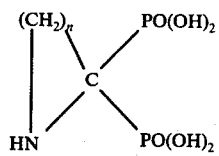

in which $n$ is an integer of from 3 to 5, or a water-soluble salt thereof, in an amount of from 0.01% to 5% by weight, preferably from 0.1% to 2% by weight, referred to the amount of anhydrous dibasic calcium phosphate employed.

More particularly, the invention relates to a process for stabilizing anhydrous dibasic calcium phosphate against reaction with fluorine ions consisting essentially of suspending anhydrous dibasic calcium phosphate in an aqueous medium at a pH of from 5 to 10, containing from 0.01% to 5% by weight based on the content of dibasic calcium phosphate, of an azacycloalkane-2,2-diphosphonic compound selected from the group consisting of (A) compounds of the formula

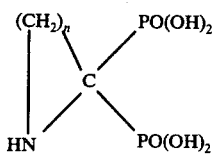

wherein $n$ is an integer from 3 to 5, and (B) water-soluble salts thereof, and separating said stabilized anhydrous dibasic calcium phosphate; as well as the stabilized dibasic calcium phosphate so produced and tooth cleaning preparations containing the same.

In carrying out the process of the invention the azacycloalkane-2,2-diphosphonic acid or its water-soluble salt, the anhydrous dibasic calcium phosphate and water may be admixed in any manner. For example, the azacycloalkane-2,2-diphosphonic acid or its water-soluble salt may be used in the mixture either as an aqueous solution or in solid form and the anhydrous dibasic calcium phosphate may be used in the mixture either as an aqueous suspension or in solid form.

The preparation of the azacycloalkane-2,2-diphosphonic acids to be used according to the present invention, or their water-soluble salts may be carried out in a simple way by reacting lactams of the formula

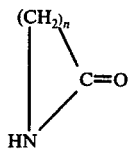

in which n represents an integer of from 3 to 5, with phosphorus trihalides or mixtures of phosphorus trihalides and phosphorous acid, hydrolyzing the reaction product and if desired converting into the salts, as are described in copending commonly-assigned U.S. patent application Ser. No. 499,000, filed Aug. 20, 1974, now U.S. Pat. No. 3,941,772.

The reaction is generally carried out at temperature of from 40° to 150° C. Suitable starting substances are, for example, pyrrolidone ($n=3$), piperidone ($n=4$) and caprolactam ($n=5$), which are readily available as commercial products.

The reaction may be carried out so that, for example, the said lactams are melted with phosphorous acid and $PCl_3$ is slowly added while stirring. The reaction product thus obtained is then hydrolyzed. However, the molten lactam can also be reacted directly with phosphorus trihalides and hydrolyzed in stages. Suitable phosphorus trihalides are especially phosphorus trichloride and phosphorus tribromide. The latter has been found particularly suitable when lactams are used without addition of phosphorous acid. The molar ratio of lactam: phosphorus compound in the reaction described ranges from 1:2 to 1:6, preferably 1:4.

The hydrolysis is suitably effected by addition of water to the reaction mixture. If desired, however, it may also be carried out in the presence of an alkali metal hydroxide, such as especially caustic soda or caustic potash.

Advantageously the azacycloalkane-2,2-diphosphonic acids may also be employed in the form of their water-soluble salts such as their alkali metal salts, especially lithium, sodium and potassium salts, and their ammonium salts. The conversion into the salts may easily be carried out by partial or complete neutralization with the corresponding bases.

The stabilization according to the present invention may either be carried out before isolation of the anhydrous dibasic calcium phosphate from the reaction medium in which it is prepared or in a later separate treatment process. The preparation of the anhydrous dibasic calcium phosphate may be effected according to processes known from the literature, for example, from calcium hydroxide and phosphoric acid. In this case it is advantageous for the preparation of the anhydrous dibasic calcium phosphate to be so controlled that rounded off crystal aggregates as homogeneous as possible are obtained.

If the stabilization is to be carried out on previously isolated anhydrous dibasic calcium phosphate which is the preferred method of production, this previously isolated anhydrous dibasic calcium phosphate is treated with an aqueous solution of the stabilizer, the pH of the solution being adjusted to from 5 to 10, preferably from 6 to 8. However, even if the stabilization is effected before isolation of the anhydrous dibasic calcium phosphate from the reaction medium, the aqueous suspension is set at a pH of 5 to 10, preferably 6 to 8, with the addition of the stabilizer. The amount of stabilizer required can easily be found by testing. It has been found that in general 0.01% to 5% by weight, preferably 0.1% to 2% by weight, based on the amount of anhydrous dibasic calcium phosphate to be stabilized is sufficient. The amount, within the indicated limits, is dependent on (a) the extent of the desired stabilization, (b) the particle size, surface and surface structure of the anhydrous dibasic calcium phosphate prepared, and (c) the time of contact between the stabilizer and the product to be stabilized. It has further been found suitable to use the water-soluble salts of azacycloalkane-2,2-diphosphonic acids, as for example, alkali metal salts, especially sodium salts. If the free acids are to be used, it may be necessary to correct for pH deviations, for example, by addition of calcium hydroxide or calcium oxide. Owing to the small amounts of the added azacycloalkane-2,2-diphosphonic acid, however, this is often unnecessary. The stabilizers to be used according to the present invention may also be used in combination with other substances, such as other stabilizers, aids to precipitation or protective colloids as, for example, with pyrophosphates, tripolyphosphates and other polymeric phosphates, polysilicates, polycarboxylates, lignin derivatives, gums and polysaccharides.

Azacycloalkane-2,2-diphosphonic acids of the above-mentioned general formula which are also substituted on the nitrogen atom also show a stabilizing action, but this is substantially less and, therefore, of little technical interest.

The present invention relates primarily to the preparation of an anhydrous dibasic calcium phosphate stabilized against reaction with fluorine ions, for use in tooth cleaning preparations. Such stabilized products, however, may also be advantageous in other fields of application. The tooth cleaning preparations to be prepared according to the present invention may contain, in addition to the stabilized anhydrous dibasic calcium phosphate serving as polishing material, the usual constituents such as, for example, thickeners, surface-active compounds or tensides, emulsifiers, bactericides, and flavoring substances. A toothpaste is the preferred form of the tooth cleaning preparations with a content of stabilized anhydrous dibasic calcium phosphate according to the present invention.

Toothpastes are generally pasty preparations based on water, which contain thickeners, wetting and foaming agents, moisture-retention agents, polishing, scouring or cleaning substances, aroma-imparting substances, taste correctors, antiseptic and other substances valuable as mouth cosmetics. The content of polishing substances in the toothpastes, i.e., the content of the anhydrous dibasic calcium phosphate which is to be used according to the present invention and which is stabilized against reaction with fluorine ions, will generally vary from 25% to 60% by weight, referred to the total mass of the toothpaste. The wetting and foaming agents employed are especially soap-free anionic surface-active compounds such as fatty alcohol sulfates, for example, sodium lauryl sulfate, monoglyceride sulfates, sodium lauryl sulfoacetate, sarcosides, taurides and other anionic surface-active compounds which do not affect the taste, in amounts from 0.5% to 5% by weight. For the preparation of the binder for toothpaste, all thickeners usual for this purpose may be used, such as hydroxyethylcellulose, sodium carboxymethylcellulose, tragacanth, carrageen moss, agar-agar and gum arabic, as well as additionally finely divided silicic acids, all in amounts of from 0.1% to 5% by weight of the whole toothpaste. As moisture-retention means, glycerine and sorbitol are of principal importance, in amounts which may be up to one-third or from 5% to 33⅓% by weight of the whole toothpaste. Water is also present in amounts of from 10% to 50% by weight of the whole toothpaste. With toothpowders, the water, thickeners and moisture-retention means are omitted. The desired aroma and taste requirements can be attained by an addition of essential oils such as peppermint, clove, wintergreen and sassafras oils, as well as by sweetening agents, such as saccharin, dulcin, dextrose or laevulose.

An essential further component of the tooth cleaning preparation to be prepared according to the present invention comprises the fluorine-containing compounds serving for the control of caries or for caries prophylaxis. These are present in amounts of from 0.01% to 2% measured as fluorine ions of the whole tooth cleaning preparations.

Fluorides against which the anhydrous dibasic calcium phosphate is stabilized are, for example, sodium fluoride, potassium fluoride, aluminum fluoride, ammonium fluoride, monoethanolamine-hydrofluoride, hexadecylamine-hydrofluoride, oleylamine-hydrofluoride, N,N',N'-tri-(polyoxyethylene)-N-hexadecyl-propylenediamine-dihydrofluoride, bis-(hydroxyethyl)-amino-propyl-N-hydroxyethyl-octadecylamine-dihydrofluoride, magnesium aspartate-hydrofluoride, and tin fluoride. Also fluorine compounds in which the fluorine is present primarily in a preponderantly non-ionic bond, which, however, may split off fluoride, for example, by hydrolysis or other chemical reactions, such as sodium monofluorophosphate, potassium monofluorophosphate, magnesium monofluorophosphate, indium fluorozirconate, zirconium hexafluorogermanate, in combination with the anhydrous dibasic calcium phosphate treated according to the present invention are protected from undesired loss of fluorine.

In the case of further cleaning and filling substances possibly also used in the tooth cleaning preparations, naturally those are preferred which themselves also do not inactivate fluoride, as for example, plastics particles, silica gels or pyrogenic silicic acids, or inorganic substances covered with polymers, waxes or other means or made compatible towards fluoride in any other way.

With reference to the other constituents it is naturally advisable to also choose those which do not inactivate the fluoride, in order that the advantage attained with the cleaning bodies according to the present invention is not reduced or eliminated, otherwise no special limits are set to the formulation of the tooth cleaning preparations.

Since the preparation of the product stabilized against the reaction with fluorine ions is generally effected by treatment of a previously isolated anhydrous dibasic calcium phosphate with an aqueous solution of the stabilizer, it is, of course, also possible to stabilize an anhydrous dibasic calcium phosphate present in an already finished toothpaste subsequently against the reaction with fluorine ions by an addition thereto of salts of azacycloalkane-2,2-diphosphonic acids. Such measures may be employed in special circumstances, but should remain confined to exceptions, since the results of such a difficultly controllable treatment in a heterogeneous system like a toothpaste is not always fully guaranteed.

The following Examples further illustrate the present invention, without however being restricted thereto.

EXAMPLES

Firstly the preparation of some azacycloalkane-2,2-diphosphonic acids to be used as stabilizers according to the present invention is described.

STABILIZER A

Preparation of azacyclopentane-2,2-diphosphonic acid $(n=3)$

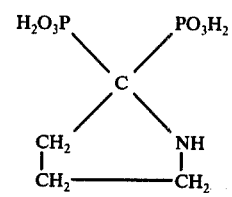

85.0 gm (1.0 mol) of 2-pyrrolidone and 164 gm (2.0 mol) of $H_3PO_3$ were melted at 80° C. 176 ml (2.0 mol) of $PCl_3$ were dropped in with stirring. The mixture was stirred for a further 3 hours and left overnight at 70° C. Then it was hydrolyzed with 3 liters of $H_2O$. The solution was boiled with activated charcoal and after filtration, the reaction product was precipitated with acetone. The white substance was dissolved in water and passed through a cation exchanger. Threafter the solution was concentrated and the substance isolated by addition of ethanol. The yield of crystalline azacyclopentane-2,2-diphosphonic acid was 95 gm Δ 41% of theory.

The molecular weight of the compound was determined titrimetrically as 230 (calculated 231.09).

In the infra-red spectrum the compound showed a $\delta_{NH}$ band at 1615 cm$^{-1}$ and had a melting point of 277° C.

STABILIZER B

Preparation of azacyclohexane-2,2-diphosphonic acid $(n=4)$

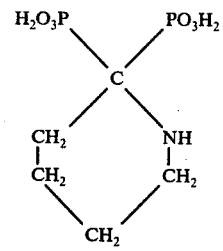

49.5 gm (0.5 mol) of 2-piperidone and 82 gm (1.0 mol) of $H_3PO_3$ were melted at 70° C and, as described in the case of Stabilizer A, reacted with 88 ml of $PCl_3$. The reaction mixture was similarly worked up. The yield of crystalline azacyclohexane-2,2-diphosphonic acid was 28 gm, 21% of theory.

After drying at 60° C in a drying oven, the compound was isolated as the monohydrate. The titrimetrically determined molecular weight is 261 (calculated 263.1).

The anhydrous compound was obtained after drying at 80° C over $P_2O_5$. The infra-red spectrum showed the $\delta_{NH}$ band at 1585 cm$^{-1}$, m.p. 249° C.

STABILIZER C

Preparation of azacycloheptane-2,2-diphosphonic acid
(n=5)

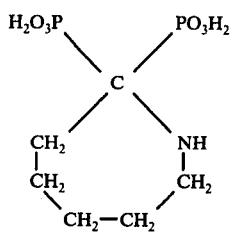

113 gm (1.0 mol) of caprolactam and 164 gm (2.0 mol) of H₃PO₃ were heated at 100° C to give a clear melt. After cooling to 70° C, the mixture was further reacted with 176 ml (2.0 mol) of PCl₃, as described for Stabilizer A. The reaction mixture was similarly worked up. The yield of crystalline azacycloheptane-2,2-diphosphonic acid, sparingly soluble in water, was 84 gm Δ 32% of theory.

After drying at 80° C in a vacuum drying oven the aazcycloheptane-2,2-diphosphonic acid had a molecular weight of 260, obtained titrimetrically (calculated 259.1).

In the infra-red spectrum the compound showed the $\delta_{NH}$ band at 1610 cm$^{-1}$, m.p. 257° C.

The following Examples serve to demonstrate the superior activity of the azacycloalkane-2,2-diphosphonic acids to be used as stabilizers according to the present invention. In these the products stabilized according to the present invention were not only compared with untreated anhydrous dibasic calcium phosphate, but also with products which were obtained by treatment with other structurally different phosphonic acids.

In order to be able to truly compare the individual experiments it is not only necessary in the measurements to keep, for example, the parameters of temperature, pH, amount of anhydrous dibasic calcium phosphate and the solution, constant, but the same anhydrous dibasic calcium phosphate should also always be used.

For the investigations a relatively large amount of crystalline anhydrous dibasic calcium phosphate was prepared from calcium hydroxide and phosphoric acid which had the following particle size distribution:

| Particle Size in μ | Percentage |
|---|---|
| <5 | 24 |
| 5 to 10 | 43 |
| 10 to 20 | 19 |
| >20 | 14 |

The preparation of the anhydrous dibasic calcium phosphate was carried out in the following way:

4.9 kg of 40% phosphoric acid were placed in a closed, heatable stirred apparatus and heated to 100° C. To this over the course of about 4 hours a suspension of 1.32 kg of calcium hydroxide and 4.12 kg of water were added dropwise. The phosphate formed was filtered off by suction, suspended again in water, and the suspension was made neutral with hydrochloric acid, filtered again and dried. The yield of anhydrous dibasic calcium phosphate was 2.2 kg.

EXAMPLE 1

32 gm of an anhydrous dibasic calcium phosphate having a particle size distribution up to 30 μ, prepared as previously described, were treated in 100 ml of a phosphate buffer solution at a pH of 7.5 with 97.5 mg of azacycloheptane-2,2-diphosphonic acid (0.3% by weight based on the phosphate). The suspension was held for 24 hours at room temperature, then filtered and dried.

30 gm of the product thus stabilized were then suspended at 40° C in 100 ml of a 10$^{-1}$ molar sodium fluoride solution, prepared by dissolving sodium fluoride in phosphate buffer solution at pH 7.

The decrease of the fluorine ion content of the solution to 10% of the starting value was followed and the time recorded (Orion Research Digital-pH/mV, Model 701 with recorder).

The experiment was so arranged that over the experimental period no concentration of the solution by evaporation of the solvent could take place.

Similarly samples were measured which were treated for stabilization with the following phosphonic acids:

0.3% amino-tris-(methylenephosphonic acid)
0.3% 1-hydroxyethane-1,1-diphosphonic acid
0.3% ethylenediamine-tetra-(methylenephosphonic acid)
0.3% methylphosphonosuccinic acid (2-phospho-propane-1,2-dicarboxylic acid).

Moreover, a sample was measured which had been similarly prepared, but without addition of a phosphonic acid stabilizer.

The measured results obtained are shown in the following Table 1.

TABLE 1

| Anhydrous CaHPO₄ Treated With 0.3% of the following | Fluorine Ion Reduction to 10% in Hours |
|---|---|
| Azacycloheptane-2,2-diphosphonic acid | 5.0 |
| Amino-tris-(methylenephosphonic acid) | 0.25 |
| 1-Hydroxyethane-1,1-diphosphonic acid | 0.8 |
| Ethylenediamine-tetra-(methylenephosphonic acid) | 0.66 |
| Methylphosphonosuccinic acid | 0.2 |
| Untreated | 0.2 |

The results show clearly the superior stabilizing action of the azacycloalkane-2,2-diphosphonic acids to be used according to the present invention.

EXAMPLE 2

Anhydrous dibasic calcium phosphate samples which had been treated with 0.75% and 1.25% by weight of the phosphonic acids mentioned in Example 1 were prepared and measured, according to the particulars given in Example 1. The following Table 2 contains the results.

TABLE 2

| Anhydrous CaHPO₄ Treated With the following | Fluorine Ion Reduction to 10% in Hours | |
|---|---|---|
| | 0.75% addition | 1.25% addition |
| Azacycloheptane-2,2-diphosphonic acid | 94 | 161 |
| Amino-tris-(methylenephosphonic | | |

TABLE 2-continued

| Anhydrous CaHPO₄ Treated With the following | Fluorine Ion Reduction to 10% in Hours | |
|---|---|---|
| | 0.75% addition | 1.25% addition |
| acid) | 0.65 | 0.4 |
| 1-Hydroxyethane-1,1-diphosphonic acid | 2.2 | 1.8 |
| Ethylenediamine-tetra-(methylene-phosphonic acid) | 1.1 | 0.6 |
| Methylphosphonosuccinic acid | 0.2 | 0.2 |
| Untreated | 0.2 | 0.2 |

The example shows still more clearly than Example 1 the superior stabilizing action of the azacycloalkane-2,2-diphosphonic acids to be used according to the present invention.

EXAMPLE 3

An anhydrous dibasic calcium phosphate sample was prepared and measured according to Example 1, which had been treated with 0.3% and 0.75% by weight of azacyclopentane-2,2-diphosphonic acid. The reduction of fluorine ion to 10% of the starting value did not occur until after 14 hours at the 0.3% level and 168 hours at the 0.75% level.

EXAMPLE 4

Two similar toothpastes were prepared. One contained untreated anhydrous dibasic calcium phosphate as a polishing material, and the other an anhydrous dibasic calcium phosphate treated with 0.75% of azacycloheptane-2,2-diphosphonic acid. Both phases also contained 0.1% of fluoride as sodium fluoride.

After 16 days storage at 50° C, soluble fluoride could no longer be detected in the paste with untreated polishing material, while in the paste with stabilized polishing material 68% of the fluoride was still present after 50 days.

In the following examples formulations for tooth cleaning preparations are given which contain anhydrous dibasic calcium phosphate stabilized according to the present invention as a polishing material.

EXAMPLE 5

Composition of a toothpaste according to the present invention

| | Parts by Weight |
|---|---|
| Glycerine | 30.0 |
| Water | 18.0 |
| Sodium carboxymethylcellulose | 1.0 |
| Anhydrous dibasic calcium phosphate stabilized with 1% of azacycloheptane-2,2-diphosphonic acid | 36.0 |
| Insoluble sodium metaphosphate | 10.0 |
| Sodium lauryl sulfate | 1.0 |
| Pyrogenic silicic acid | 1.5 |
| Sodium monofluorophosphate | 0.5 |
| Essential oils | 1.5 |
| Saccharin Sweetener | 0.5 |

Instead of Stabilizer C used in the above formulation for stabilizing the anhydrous dibasic calcium phosphate, Stabilizers A and B can be used in the same amounts with the same good results.

EXAMPLE 6

Composition of a toothpaste according to the present invention.

| | Parts by Weight |
|---|---|
| Anhydrous dibasic calcium phosphate stabilized with 1% of azacyclopentane-2,2-diphosphonic acid | 40.0 |
| Water | 29.3 |
| Glycerine | 18.0 |
| sorbitol | 7.0 |
| Sodium carboxymethylcellulose | 1.0 |
| Pyrogenic silicic acid | 1.5 |
| Sodium lauryl sulfate | 1.0 |
| Essential oils | 1.5 |
| Saccharin sweetener | 0.5 |
| Sodium fluoride | 0.2 |

Instead of the Stabilizer A used in the above formulation for the stabilization of the anhydrous dibasic calcium phosphate, Stabilizers B and C may be used in the same amounts with the same good results.

EXAMPLE 7

Composition of a tooth powder according to the present invention.

| | Parts by Weight |
|---|---|
| Anhydrous dibasic calcium phosphate, stabilized with 1% of azacycloheptane-2,2-diphosphonic acid | 50.0 |
| Precipitated chalk | 30.0 |
| Finely divided silicic acid | 10.0 |
| Milk sugar | 4.0 |
| Precipitated magnesium carbonate | 3.5 |
| Titanium dioxide | 1.0 |
| Tannin | 1.0 |
| Sodium monofluorophosphate | 0.5 |

Instead of the Stabilizer C used in the above formulation for the stabilization of the anhydrous dibasic calcium phosphate, Stabilizers A and B may be used in the same amount with the same good results.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for stabilizing anhydrous dibasic calcium phosphate against reaction with fluorine ions consisting essentially of suspending anhydrous dibasic calcium phosphate in an aqueous medium at a pH of from 5 to 10, containing from 0.01% to 5% by weight based on the content of dibasic calcium phosphate of an azacycloalkane-2,2-diphosphonic compound selected from the group consisting of (A) compounds of the formula

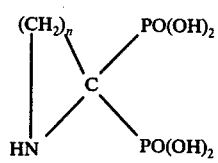

wherein $n$ is an integer from 3 to 5, and (B) water-soluble salts thereof, and separating said stabilized anhydrous dibasic calcium phosphate.

2. The process of claim 1 wherein said pH is between 6 to 8.

3. The process of claim 1 wherein the amount of said azacycloalkane-2,2-diphosphonic compound is from 0.1% to 2% by weight based on the content of anhydrous dibasic calcium phosphate.

4. The process of claim 1 wherein said water-soluble salts are selected from the group consisting of the alkali metal salts and ammonium salts.

5. An anhydrous dibasic calcium phosphate stabilized against reaction with fluorine ions by an azacycloalkane-2,2-diphosphonic acid produced by the process of suspending anhydrous dibasic calcium phosphate in an aqueous medium at a pH of from 5 to 10, containing from 0.01% to 5% by weight based on the content of dibasic calcium phosphate of an azacycloalkane-2,2-diphosphonic compound selected from the group consisting of (A) compounds of the formula

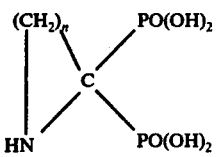

wherein $n$ is an integer from 3 to 5, and (B) water-soluble salts thereof, and separating said stabilized anhydrous dibasic calcium phosphate.

* * * * *

UNITED STATES PATENT OFFICE
CERTIFICATE OF CORRECTION

Patent No. 4,108,961　　　　　　　　Dated　Aug. 22, 1978

Inventor(s)　WALTER PLOGER and CLAUS GUTZSCHEBAUCH

It is certified that error appears in the above-identified patent and that said Letters Patent are hereby corrected as shown below:

Column 10, line 12,　　"sorbitol" should be --Sorbitol--

Signed and Sealed this

Third Day of April 1979

[SEAL]

Attest:

RUTH C. MASON
Attesting Officer

DONALD W. BANNER
Commissioner of Patents and Trademarks